(12) United States Patent
Malowaniec

(10) Patent No.: US 8,523,835 B2
(45) Date of Patent: Sep. 3, 2013

(54) PANT-TYPE DISPOSABLE ABSORBENT HYGIENE PRODUCT

(75) Inventor: Krzysztof D. Malowaniec, Heidenheim (DE)

(73) Assignee: Paul Hartmann AG, Heidenheim (DE)

( * ) Notice: Subject to any disclaimer, the term of this patent is extended or adjusted under 35 U.S.C. 154(b) by 216 days.

(21) Appl. No.: 12/926,574

(22) Filed: Nov. 26, 2010

(65) Prior Publication Data

US 2011/0125126 A1 May 26, 2011

Related U.S. Application Data

(63) Continuation of application No. 11/922,507, filed as application No. PCT/EP2006/006192 on Jun. 27, 2006, now abandoned.

(30) Foreign Application Priority Data

Jun. 29, 2005 (DE) .......................... 10 2005 030 182

(51) Int. Cl.
*A61F 13/49* (2006.01)

(52) U.S. Cl.
USPC ............ 604/385.28; 604/385.27; 604/385.26; 604/385.25; 604/385.24; 604/285.29

(58) Field of Classification Search
USPC ....................................... 604/385.25–385.28
See application file for complete search history.

(56) References Cited

U.S. PATENT DOCUMENTS

| | | | | |
|---|---|---|---|---|
| 5,904,675 A * | 5/1999 | Laux et al. | ............... | 604/385.29 |
| 6,391,013 B1 * | 5/2002 | Suzuki et al. | ............ | 604/385.27 |
| 6,602,238 B2 * | 8/2003 | Takei et al. | .............. | 604/385.26 |
| 7,000,260 B2 * | 2/2006 | Rajala et al. | ...................... | 2/400 |
| 7,112,186 B2 | 9/2006 | Shah | | |
| 2005/0075618 A1 * | 4/2005 | Kenmochi et al. | ........ | 604/385.27 |

FOREIGN PATENT DOCUMENTS

| | | |
|---|---|---|
| JP | 2002-065 732 | 3/2002 |
| JP | 2003-532 495 | 11/2003 |

* cited by examiner

*Primary Examiner* — Susan Su
(74) *Attorney, Agent, or Firm* — Paul Vincent

(57) ABSTRACT

A pant-type disposable absorbent hygiene article (2), comprises a waist edge (20), continuous in the circumferential direction thereof and forming a waist opening, and leg openings (8*a,b*), a front piece (6) and a back piece (4) having longitudinal side edge sections (16,18), and a crotch region (10), disposed between the front piece (6) and the back piece (4). The waist edge (20), continuous in the circumferential direction thereof, and the leg openings (8*a,b*) are produced by joining, on the manufacture end, the longitudinal side edge sections (16,18) of a front piece (6) and a back piece (4). The hygiene article also comprises an absorbent body (22). Every leg opening (8*a,b*) has an elastic leg opening section (81). Cuff elements (7) are provided on both sides of the absorbent body (22) and extend in the longitudinal direction (28) thereof, each cuff element (7) having an elastic cuff element section (9), and a) every cuff element (7) having at least one non-elastic cuff element section (11) and, when the product is placed on the body of the user, the elastic leg opening section (81) crosses the respective non-elastic cuff element section (11) or b) the length of the respective cuff element (7) being chosen in such a manner that, when the product is placed on the body of the user, the elastic leg opening section (81) does not cross the respective cuff element (7).

21 Claims, 2 Drawing Sheets

PANT-TYPE DISPOSABLE ABSORBENT HYGIENE PRODUCT

This application is a continuation of Ser. No. 11/922,507 filed on Dec. 19, 2007 as the national stage of PCT/EP2006/006192 filed on Jun. 27, 2006 and also claims Paris Convention priority to DE 10 2005 030 182.7 filed Jun. 29, 2005 the entire disclosures of which are hereby incorporated by reference.

BACKGROUND OF THE INVENTION

The invention concerns a pant-type disposable absorbent hygiene article comprising a hip edge which forms a hip opening and is continuously closed in the peripheral direction, leg openings, wherein the hip edge, which is continuously closed in the peripheral direction, and the leg openings are formed by connecting the longitudinal side edge sections of a front part and a rear part during manufacture, an absorbent body, at least one elastic leg opening section, and cuff elements on both sides of the absorption core, which comprise an elastic cuff element section.

Conventional pant-type absorbent hygiene articles of this type mostly comprise a plurality of elastification means, often in the form of rubber-elastic threads which are connected in a pre-tensioned state to chassis material, usually by glue. A hip edge area is thereby usually and preferably continuously elastified in the peripheral direction. Conventional diaper pants also have elastification means in the front area and rear area. The peripheral areas that surround the leg openings or form the leg openings are also elastic, at least in sections, in order to ensure largely tight abutment of the hygiene article on the skin surface of the user in order to prevent body fluids from escaping towards the side. Upright cuff elements, which offer further lateral outlet protection in addition to the elastic leg openings, are also used in conventional diaper pants and are e.g. disclosed in EP-1 184 017 A1, EP 1 199 058 A1, EP 1 308 148 A2.

Abutment of elastified pretensioned areas on the skin surface in the area of the leg openings or the cuff elements often causes skin irritation due to friction or the action of force of mostly thread-shaped elastification means. When the area within the hygiene article is additionally moist due to body fluids or perspiration, this problem is even aggravated. It is even more aggravated by increasing activity, i.e. movement, of the user.

Departing therefrom, it is the object of the present invention to improve the wear comfort of absorbent hygiene articles of the above-mentioned type and, in particular, reduce skin irritation.

SUMMARY OF THE INVENTION

This object is achieved with a pant-type disposable absorbent hygiene article, the article comprising the following elements whose mutual geometric orientation is described when worn by an upright user:
means defining a hip edge, said hip edge forming a hip opening which is continuously closed in a peripheral direction;
means defining a first leg opening;
means defining a second leg opening;
a front part having longitudinal side edge sections;
a rear part having longitudinal side edge sections;
a crotch area disposed between said front part and said rear part;
a first substantially vertical seam extending between said hip opening and said first leg opening;
a second substantially vertical seam extending between said hip opening and said second leg opening, wherein said hip opening and said first and second leg openings are formed by connecting said longitudinal side edge sections of said front part and said rear part to each other at said first and said second seams during manufacture of the article;
an absorbent body subtending said crotch area and disposed between said first and said second leg openings;
a first elastic leg opening section extending upwardly in a curved manner along a rear portion of said first leg opening and curving about an upper portion of said first leg opening to extend downwardly along a front portion of said first leg opening towards said crotch area;
a second elastic leg opening section extending upwardly in a curved manner along a rear portion of said second leg opening and curving about an upper portion of said second leg opening to extend downwardly along a front portion of said second leg opening towards said crotch area;
a first cuff element extending in a longitudinal direction along said absorbent body proximate said first leg opening, said first cuff element having at least one non-elastic cuff element section and a first elastic cuff element section, wherein said first elastic cuff element section is longitudinally disposed between but does not cross said first elastic leg opening section; and
a second cuff element extending in a longitudinal direction along said absorbent body proximate said second leg opening, said second cuff element having at least one non-elastic cuff element section and a second elastic cuff element section, wherein said second elastic cuff element section is longitudinally disposed between but does not cross said second elastic leg opening section.

In accordance with the invention a) each cuff element comprises at least one non-elastic cuff element section and the elastic leg opening section crosses the respective non-elastic cuff element section after application to the body of the user, or b) the longitudinal extension of the respective cuff element is dimensioned such that after application to the body of the user, the elastic leg opening section does not cross the respective cuff element.

Since the thread- or band-shaped elastification means, which are preferably used, gather or frill the materials connected thereto when being connected to these materials in the pretensioned state, they accumulate material in the relaxed state which may be unpleasant. In any case, gathered or frilled areas, i.e. elastified areas, rub greatly against the skin of the user, in particular, when the user moves, which can produce the above-mentioned skin irritation.

It has turned out in accordance with the invention that the probability that skin irritation occurs can be reduced by preventing a plurality of at least two elastic components from overlapping in an area which directly and tightly abuts the skin of the user.

In view of the fact that modern hygiene articles of this type already have a double lateral outlet protection system, it seems to be sufficient to form the cuff elements only in the central area and over a short section, or to render them elastic at least only in this central area and over a short section. This also reduces the amount of material required for the elastification means and for joining, e.g. glue.

In a first variant of the invention, a very short length of the cuff elements is disposed only in a central crotch area, such that after application of the article to the user, crossing, i.e. sectional overlapping of cuff element and elastic leg opening element is prevented.

In a second variant of the invention, each band has an elastic and a non-elastic cuff element section, and these sections are arranged such that the elastic leg opening sections cross the cuff elements in their non-elastic section.

Since diaper pants usually comprise elastic leg opening sections both in the front and rear leg opening area, in a further development of the invention, the respective cuff element has at least two sections which are not elastified. These are closer to the respective hip edges than the elastic cuff element section and are arranged at that location where the elastic leg opening section and the cuff element overlap, i.e. cross, when the article has been applied to the user.

In a further development of the invention, each cuff element is provided with several, i.e. at least two, elastic cuff element sections. In this case, the elastic cuff element sections are spaced apart from each other by non-elastic cuff element sections. This is advantageous in that the cuff elements can be arranged more flexibly and their length can be dimensioned more flexibly. If e.g. very long absorbent bodies are to be used, secure standing up of the cuff elements can be ensured only by a correspondingly long elastification section. In this case, the non-elastified band sections can form areas between two elastified band sections, in which the elastic leg opening sections can cross the cuff elements after application of the article to the user.

The elastic cuff element sections and/or the elastic leg opening sections are conventionally preferably formed by non-woven or foil materials which are elastified, in particular, by thread or band-shaped elastification means such as rubber or polyether polyurethane or polyester polyurethane threads. Towards this end, the elastification means are preferably fixed in the pretensioned state to the non-woven or foil materials (stretch bonding) such that the restoring force of the elastification means elastically gathers the corresponding sections after release of the pretension.

The non-elastic cuff element section(s) is/are obtained, in particular, in that no elastification means are provided at that location. This reduces material costs and prevents most reliably the problems of overlapping after application of the diaper, which can cause skin irritations as described above.

The non-elastic cuff element section(s) can also be obtained, in particular, in that the elastification means are relaxed in these sections.

The non-elastic cuff element section(s) can be obtained, in particular, in that the elastification means in these sections are not connected to the cuff elements, such that with the above-mentioned "stretch-bonding" and subsequent release of tension, the elastification means in these sections are disposed without tension and thereby exert no force on the cuff elements such that the cuff elements are not gathered in these sections. Reference is hereby made to the disclosure of DE 2 649 948 A1 with regard to elastification of flat material components, only in sections, through thread or band-shaped elastification means.

The inventive hygiene article preferably has an outer covering that forms the diaper chassis, comprising a front part, a rear part and an intermediate crotch part that comprises the leg openings. The outer covering is preferably formed from non-woven material and/or foil materials. In order to ensure air and/or water vapor circulation, only non-woven materials are preferably used. The outer covering can be designed, in particular, in the form of a continuous material section which extends from a front hip edge to a rear hip edge. In another feasible and advantageous variant, the outer covering is formed from a front covering part and a rear covering part, as e.g. already taught in WO 2004 060238. In this case, the front covering part and the rear covering part are spaced apart from each other in the crotch area. The absorption core of this embodiment is connected to a front area at the front covering part and to a rear area at the rear covering part, such that the front covering part and the rear covering part are only indirectly connected to each other via the absorption core, thereby forming the chassis.

In a further development of this embodiment, the side of the absorption core remote from the body of the respective front or rear area, may be connected to the side of the respective covering part close to the body. In an alternative further development, the arrangement may be reversed, i.e. the side of the absorption core close to the body of the front or rear area can be connected to the side of the respective covering part remote from the body. The absorption core may finally also be disposed with its front and/or rear areas like a sandwich between the layers, remote and close to the body, of the front and/or rear covering parts, which have several layers in this case, and be connected thereto.

When the outer covering is continuous, the absorption core may be disposed as an integral component of the outer covering, in particular, between a covering layer close to the body and a covering layer remote from the body.

In a preferred embodiment, the side of the absorbent body remote from the body, is disposed on the layer of the outer covering close to the body, and preferably fixed thereto, at least in sections, through adhesive, such as hot melt adhesive or other joining methods, such as thermal welding.

The absorption core comprises at least one storage core with materials absorbing body liquids, such as natural or synthetic fibers, in particular, cellulose fibers, preferably in the form of cellulose fluff. The storage core also preferably comprises super-absorbent materials (SAP), in particular, on the basis of surface-linked, partially neutralized polyacrylates. The absorbent body is preferably covered by a top sheet which is liquid-permeable at least in sections, and moreover preferably backed by a back sheet which is impermeable to liquids, at least in sections, during use. The top sheet comprises, in particular, non-woven materials or foil materials having openings. The back sheet comprises, in particular, a foil, in particular of a thickness of maximally 15 μm. The back sheet can also advantageously contain or consist of non-woven materials, which are fluid-tight but permeable to water vapor during use, such as meltblown layers (M) and spunbond layers (S), in particular laminates of meltblown and spunbond layers, such as SM or SMS or SMMS laminates. The back sheet comprises, in particular, a foil which is fluid tight during use but at the same time breathable, i.e. water vapor permeable, in particular microporous. The water vapor permeability of the back sheet is, in particular, at least 300 $g/m^2/24$ h, moreover, in particular, at least 1000 $g/m^2/24$ h, in particular at least 2000 $g/m^2/24$ h, moreover, in particular, at least 3000 $g/m^2/24$ h, moreover, in particular, at least 4000 $g/m^2/24$ h, moreover in particular at most 6000 $g/m^2/24$ h, measured in accordance with DIN 53 122-1 (edition: 2001-08).

The cuff elements extend on both sides of the absorption core and are fixed, in particular, with their proximal edges on a respective longitudinal edge of the side of the absorption core close to the body, in particular the top sheet. In an alternative further development of the invention, the proximal edges of the cuff elements are fixed on both sides outside of the absorption core, i.e. on the side of the outer covering close to the body.

The distal edges which stand up, at least in sections, towards the user, preferably have elastification means, in particular, thread- or band-shaped elastification means of the above-mentioned type. In an alternative embodiment, the cuff elements comprise or consist of massively elastic material, such as an elastic foil or an elastic non-woven material.

The distal edge of the cuff elements is preferably inclined to the inside towards the longitudinal axis of the hygiene article. This is ensured, in particular, in that the distal edge of the cuff elements is fixed in one or both end sections towards the inside on the side of the absorption core facing the body, in particular to the top sheet. By fixing the end sections of the cuff elements over a sufficiently large section on the absorption core, in a preferred embodiment, the elastic effect of this section can be stopped simultaneously, wherein this fixed end section is to be regarded as coinciding with a non-elastified band section.

The leg openings of an inventive hygiene article have at least one elastic leg opening section. A primary elastic leg opening section of each leg opening preferably extends in the flat state prior to connection of the longitudinal side edge sections by the producer, starting from a longitudinal side edge of the front part or rear part of the article in a curve along a periphery of the respective leg opening towards a crotch center line. The curved arrangement of the elastic leg opening section specifically supports the anatomically designed adjustment of the hygiene article. A secondary elastic leg opening section is preferably provided adjacent the first leg opening section.

The secondary leg opening section is preferably elastified by thread or band-shaped elastification means of the above-mentioned type, and extends in particular substantially parallel to the central longitudinal axis (L). This permits formation of the secondary leg opening section by elastification means which are connected on both sides to the absorption core. In a preferred embodiment, the secondary elastic leg opening section can thus be elastified by the elastic longitudinal edges of the absorption core. In an alternative fashion, the secondary elastic leg opening section can be elastified by elastification means which are disposed on both sides outside of the absorption core, i.e. directly connected to the outer covering.

As viewed again in the flat state prior to connection of the longitudinal side edge sections by the manufacturer, a further, tertiary elastic leg opening section of each leg opening extends from a longitudinal side edge of the front part or rear part of the article on a curve along a periphery of a respective leg opening towards a center crotch line.

In a preferred embodiment, each leg opening comprises the above-described primary, secondary and tertairy elastified leg opening sections, such that the first and third leg opening sections have a considerable separation in the longitudinal direction of the hygiene article, in particular, a separation of at least 10 cm, in particular at least 15 cm, moreover in particular at least 18 cm, moreover in particular at most 30 cm. The secondary elastic leg opening sections are disposed such that they bridge this separation at least in sections. In order to prevent mutual disturbance of the elastic effects of the elastic leg opening sections and material accumulation that produces skin irritations, the end areas of the respective secondary elastic leg opening section are preferably spaced apart from the end areas of the respective primary and/or tertiary elastic leg opening sections, preferably by a length A, wherein the length A is preferably 10 mm, in particular at least 15 mm, moreover, in particular, at least 18 mm.

In order to prevent overlapping or crossing of the elastic leg opening sections with the elastic cuff element sections in accordance with the invention, the mentioned sections are advantageously arranged and dimensioned in particular in that the longitudinal extension of the elastic cuff element section is at most 8 cm, in particular at most 6 cm, in particular at most 4 cm, in particular at most 2 cm larger than the longitudinal extension of the separation C between the first elastic leg opening section and the third elastic leg opening section. In one particularly advantageous arrangement, the longitudinal extension of the elastic cuff element section is equal to or shorter than the longitudinal extension of the separation C between the first elastic leg opening section and the third elastic leg opening section by at least 1 cm, moreover by at least 2 cm, moreover by at most 4 cm.

In another advantageous embodiment, elastification means are provided between the hip edge and the crotch area which extend substantially in a transverse direction, in order to improve the fit of the hygiene article in view of tight arrangement on the body. An elastification means of this type in the area of the absorbent body can produce a desired contraction of the absorptive body in the crotch area.

In another advantageous embodiment, elastification means are provided in the crotch area which extend substantially in a transverse direction. It may be desired that the absorbent body is narrow in the crotch area, but still provides sufficient absorptive capacity, i.e. absorbent material. By contraction, the surface density in this area can be increased in order to provide this area with a large absorption capacity. Moreover, the elastification means that extend transversely in the crotch area shape the hygiene article, thereby advantageously generating a shell shape in the crotch area.

The elastification means which extend(s) in the crotch area substantially in a transverse direction may be formed separately from those elastification means which elastify the leg openings. In accordance with a further embodiment of the invention, the elastification means of the elastified leg opening section, in particular, the primary and/or tertiary elastified leg opening section advantageously merge into the elastification means of the crotch area, i.e. form the elastification means in the crotch area extending in the transverse direction in that they extend from their extension in the peripheral direction of the leg openings substantially in a transverse direction via a turning point. They can thereby branch off in a substantially continuous or also non-continuous curve, wherein a continuous curve is preferred.

If the absorption core shall not be gathered in the crotch area e.g. for appearance reasons, the elastifying effect of these elastification means can be eliminated, in particular, in an area after passing the turning point, in particular by separating them. The elastification means will then relax or rebound unless they are connected to the outer covering in this section.

Separation may also be effected e.g. by one single cut. It would, however, also be feasible and advantageous to separate the elastification means by a plurality of cuts, such that the previously continuously extending elastification means are divided into a plurality of small sections, in particular, of a length in the millimeter range, thereby losing their elastifying effect. In this case, the elastification means may also be connected to the outer covering with glue, without thereby impeding the relaxation. Single or multiple separation of the elastification means may also be effected using laser technology. In one alternative embodiment, the elastic effect of the previously extending elastification means is eliminated by application of heat and/or pressure and/or ultrasound. The application of heat and/or pressure is advantageous compared to separating cuts, since it reduces the risk that the materials forming the outer covering are also erroneously cut or perforated.

Reference is hereby made to EP 1 374 814 A1 which discloses a technology of applying heat and/or pressure for deactivating elastification means, the entire disclosure of which is hereby incorporated by reference.

Further features, details and advantages of the invention can be extracted from the attached claims and the drawing and subsequent description of preferred embodiments of the inventive hygiene article.

DESCRIPTION OF THE PREFERRED EMBODIMENT

Figure 1:
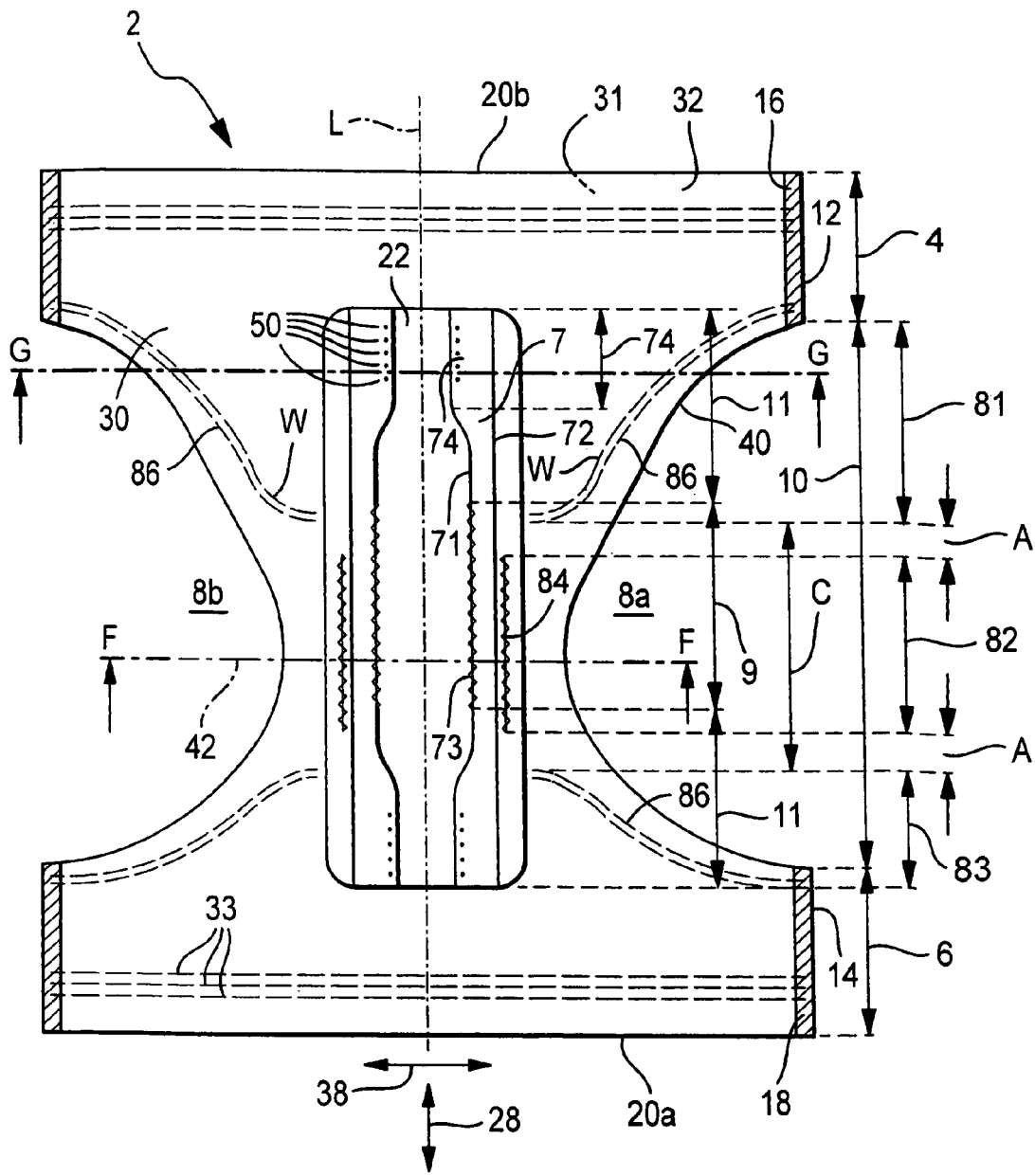
FIG. 1 shows a top view of a first embodiment of an inventive hygiene article in the flat state prior to connection of longitudinal side edge regions during manufacture.

FIG. 1 shows a hygiene article, which is designated in total with reference numeral 2, in the form of a diaper pant ("pant"), but in the flat state prior to connection of the longitudinal side edge sections during manufacture. The hygiene article comprises a rear part 4, a front part 6 and an intermediate crotch part 10 which delimits the later leg openings 8a, b. In the flat state, the rear part 4 is delimited by longitudinal side edges 12 and the front part 6 is delimited by longitudinal side edges 14. These are connected to each other to form the pant shape in the area of the hatched zones 16 and 18, e.g. by heat sealing or other conventional joining methods. In this fashion, two side seam areas of the hygiene article are formed which cannot be released without being destroyed. The readily configured hygiene article may in any case have a breaking line, in particular along these side seam areas, e.g. in the form of a tear strip in order to open the hygiene article starting from the applied state. Any closure elements, e.g. adhesive or mechanically adhering closure flaps, may additionally be provided in order to be able to close the hygiene article again after opening like a diaper. The hygiene article is produced by the manufacturer as a pant and therefore has a hip edge 20 which is closed in the peripheral direction and forms a hip opening which is limited on all sides.

Figure 2:
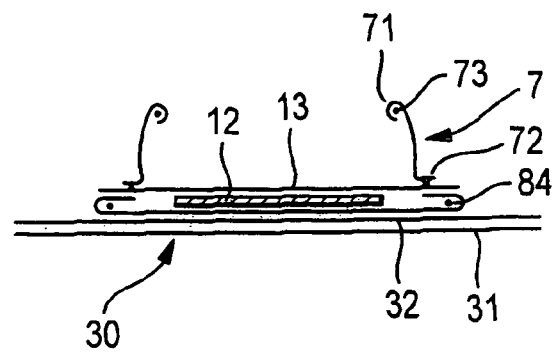
FIG. 2 shows a first sectional view of the hygiene article shown in FIG. 1 along a plane F-F.

The hygiene article 2 moreover comprises an absorbent body 22 which is designed as a functional and prefabricated unit, i.e. the absorption core has a liquid-absorbing and -storing storage core 12, a liquid-impermeable back sheet 14 and a liquid-permeable top sheet 13. The cuff elements 7 are formed from a hydrophobic non-woven material and are fixed to the top sheet 13 with their proximal edge 72 on both sides of the storage core 12 parallel to the longitudinal axis L. The respective distal edge 71 of the cuff elements 7 has an elastification means 73, i.e. an elastic rubber thread, in a section comprising the crotch center, the elastic cuff element section 9. The elastic cuff element section 9 can stand up against the skin of the user (FIG. 2) due to the restoring force of the rubber thread. The respective cuff element remains non-elastified in the direction of the front and rear hip edges 20a, 20b, and forms non-elastified sections 11. The distal edge 71 is bent inwardly at a rear and front end section 74 of the cuff element 7 and fixed to the top sheet by the ultrasound weld points 50. The absorption core also comprises elastification means 84 which are oriented parallel to the longitudinal axis L, which (FIG. 2) are fixed to the bent longitudinal edge of the back sheet by fusion adhesive. It would also be feasible to provide the arrangement of elastification means 84 directly between the top sheet 13 and the back sheet 14. The elastification means 84 are preferably disposed outside of the proximal edge 72 of the cuff elements 7, as viewed from a transverse direction 38, i.e. the elastification means 84 are disposed closer to the leg openings 8a, b than the proximal edges 72 of the cuff elements 7.

The absorption core, being a functional and prefabricated unit, is connected on its side remote from the body, i.e. the side of the back sheet 14 facing away from the body, to the side of the outer covering close to the body. The outer covering 30 forming the diaper chassis extends continuously from the front hip edge 20a to the rear hip edge 20b and comprises a two-layered non-woven laminate consisting of a non-woven layer 32 close to the body and a non-woven layer 31 remote from the body, which are connected to each other at least in sections. Elastic rubber threads 33 which are elastic in the transverse direction 38, pretensioned between the two non-woven layers 31, 32 and fixed by melt adhesive extend between the respective hip edges 20a, 20b and the start of the leg openings 8a, b. The hip edges 20a, 20b also have elastification means which extend in the transverse direction 38 (not shown herein).

There are furthermore elastification means 86 which elastify sections of the leg openings 8a, b. The elastification means 86 which are designed as rubber threads are also pretensioned between the two non-woven layers 31, 32 and fixed by fusion adhesive. The elastification means 86 extend from the longitudinal side edge 12 of the rear part 4 on a curve along a periphery 40 of the observed leg opening 8a, b towards a center crotch line 42. The elastifying effect of the elastification means 86 is not continuous up to the center crotch line 42 but limited from the longitudinal side edge 12 to a primary leg opening section 81. The elastification means 86 merge from their extension in the peripheral direction of the leg openings 8a via a turning point W substantially in the transverse direction 38. They subsequently traverse the crotch area below the absorption core 22 and extend on a mirror image path along the other second leg opening 8a on the opposite side. The elastic effect of the elastification means 86 has, however, been eliminated below the absorption core through application of pressure and heat.

Elastification means 86 also extend from the longitudinal side edge 14 of the front pat 6 along the periphery 40 of the observed leg opening 8a, b towards a center crotch line 42. The elastifying effect of the elastification means 86 in the front part 6 is not continuously provided to the center crotch line 42, but is limited, from the longitudinal side edge 12, to a tertiary leg opening section 83. The elastification means 86 merge again from their extension in the peripheral direction of the leg opening 8a via a turning point W substantially into the transverse direction 38 before they reach the center crotch line 42. They subsequently traverse the crotch area below the absorption core 22 and extend on a mirror image path along the further second leg opening 8b on the opposite side. The elastic effect of the elastification means 86 has been eliminated below the absorption core through application of pressure and heat.

The primary 81 and tertiary leg opening sections 83 therefore have a separation C of preferably 23 cm in the longitudinal direction 28.

One can also see the previously described elastification means 84 which form the secondary elastified leg opening section 82 and partially fill this separation C. A separation A of 20 mm remains, however, between the end areas of the secondary elastic leg opening section 82 and the end areas of the primary 81 and tertiary elastic leg opening section 83.

This prevents mutual disturbance of the elastic effects and also prevents accumulation of elastic material on top of each other, which can also cause skin irritations.

Figure 3:
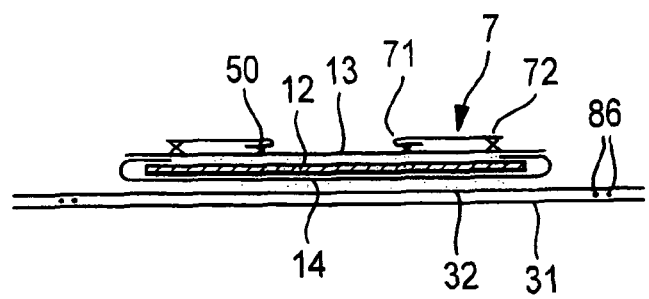
FIG. 3 shows a second sectional view of the hygiene article shown in FIG. 1 along a plane G-G.
Figure 4:
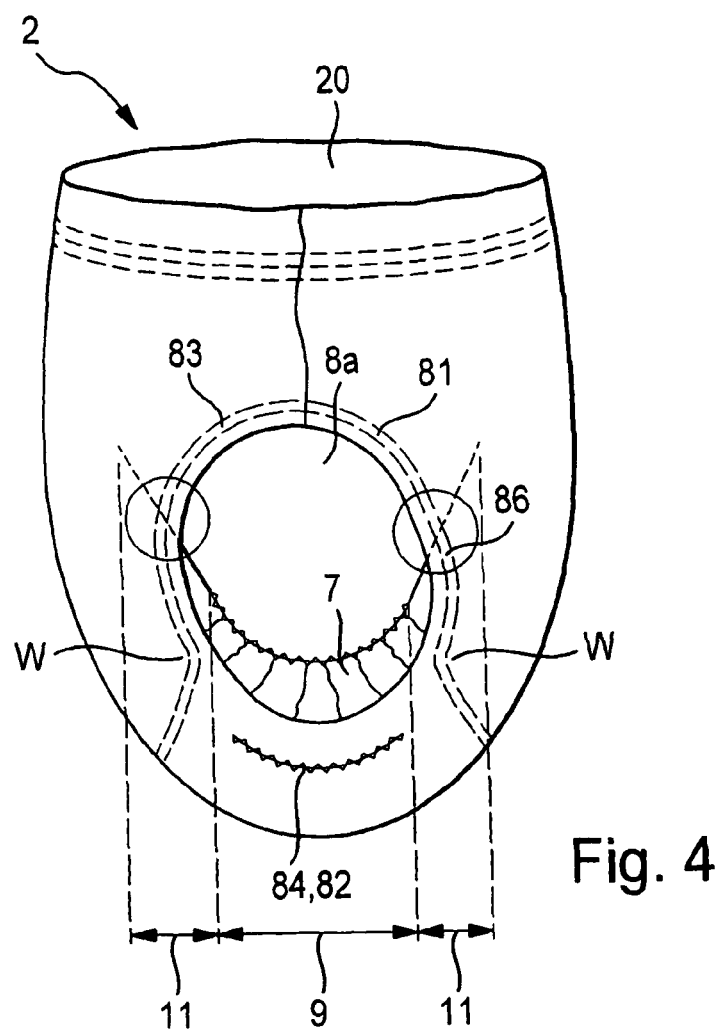
FIG. 4 shows a perspective view of an inventive diaper in the state applied to the user.

FIG. 4 shows a perspective view of the leg opening 8a illustrating the arrangement of the primary and tertiary elastic leg opening sections 81, 83 provided with elastification means, and the elastic cuff element section 9 after application of the hygiene article 2 (shown in FIGS. 1-3) to the user (not shown). The primary 81, secondary 82 and tertiary 83 elastic leg opening sections are shown around part of the leg opening 8a. The cuff elements 7 with the elastic cuff element section 9 and the non-elastic cuff element sections 11 are also shown. It is thereby reliably prevented that the elastic leg opening sections and the elastic cuff element section cross. The primary 81 and secondary 83 elastic leg openings sections cross the cuff elements 7 only on their non-elastic cuff element sections 11 within the imaginary circles indicated in FIG. 4. The material accumulation of gathered material in a region which abuts the leg of the user in a tight and tensioned fashion is reduced and thereby also the danger of skin irritations.

I claim:

1. A pant-type disposable absorbent hygiene article, the article comprising the following elements whose mutual geometric orientation is described when worn by an upright user:
   means defining a hip edge, said hip edge forming a hip opening which is continuously closed in a peripheral direction;
   means defining a first leg opening;
   means defining a second leg opening;
   a front part having longitudinal side edge sections;
   a rear part having longitudinal side edge sections;
   a crotch area disposed between said front part and said rear part;
   a first vertical seam extending between said hip opening and said first leg opening;
   a second vertical seam extending between said hip opening and said second leg opening, wherein said hip opening and said first and second leg openings are formed by connecting said longitudinal side edge sections of said front part and said rear part to each other at said first and said second seams during manufacture of the article;
   an absorbent body subtending said crotch area and disposed between said first and said second leg openings;
   a first elastic leg opening section extending upwardly in a curved manner along a rear portion of said first leg opening and curving about an upper portion of said first leg opening to extend downwardly along a front portion of said first leg opening towards said crotch area;
   a second elastic leg opening section extending upwardly in a curved manner along a rear portion of said second leg opening and curving about an upper portion of said second leg opening to extend downwardly along a front portion of said second leg opening towards said crotch area;
   a first cuff element extending in a longitudinal direction along said absorbent body proximate said first leg opening, said first cuff element having at least one non-elastic cuff element section and a first elastic cuff element section, wherein said first elastic cuff element section is longitudinally disposed between two elastic segments of said first elastic leg opening section but, as viewed from a sideward direction, does not cross any part of said first elastic leg opening section; and
   a second cuff element extending in a longitudinal direction along said absorbent body proximate said second leg opening, said second cuff element having at least one non-elastic cuff element section and a second elastic cuff element section, wherein said second elastic cuff element section is longitudinally disposed between two elastic segments of said second elastic leg opening section but, as viewed from a sideward direction, does not cross any part of said second elastic leg opening section.

2. The hygiene article of claim 1, wherein each of said first and said second cuff elements has two non-elastic cuff element sections, wherein a first non-elastic cuff element section is disposed closer to a front hip edge than said respective first or second elastic cuff element section and a second non-elastic cuff element section is disposed closer to a rear hip edge than said respective first or second elastic cuff element section.

3. The hygiene article of claim 1, wherein each of said first and said second cuff elements has one single elastic cuff element section at least a portion of which is positioned in said crotch area.

4. The hygiene article of claim 1, wherein said first or said second elastic cuff element section and/or said first or said second elastic leg opening section is elastified by thread- or band-shaped elastification means.

5. The hygiene article of claim 1, wherein said non-elastic cuff element section is obtained by separating previously extending elastification means.

6. The hygiene article of claim 5, wherein said separation is achieved by a plurality of cuts.

7. The hygiene article of claim 1, wherein said non-elastic cuff element section is obtained by eliminating an elastifying effect of a previously extending elastification means through application of heat, and/or pressure, and/or laser, and/or ultrasound.

8. The hygiene article of claim 1, wherein said non-elastic cuff element section is obtained in that elastification means extending at a location thereof are disposed without tension.

9. The hygiene article of claim 1, wherein said non-elastic cuff element section is obtained in that no elastification means are provided at least in sections at that location.

10. The hygiene article of claim 1, wherein said first and said second cuff elements have a distal and a proximal edge and said first and said second elastic cuff element section are elastified by thread- or band-shaped elastification means disposed on said distal edge.

11. The hygiene article of claim 10, wherein said absorbent body comprises a storage core, a top sheet that extends above said storage core, and a back sheet that extends below said storage core.

12. The hygiene article of claim 11, wherein a respective said distal edge of a front and/or rear end section of said first and said second cuff elements is fixed to said top sheet.

13. The hygiene article of claim 11, wherein a respective distal edge of said first and said second cuff elements is inwardly inclined towards a central longitudinal axis of the article, by inwardly disposing a respective end section towards said longitudinal axis of the article and by fixing it to said top sheet.

14. The hygiene article of claim 11, wherein a primary elastic leg opening section of each of said first and said second elastic leg opening sections is provided in a flat state prior to connection of said longitudinal side edge sections by the manufacturer, starting from a longitudinal side edge of said rear part of the article on a curve along a periphery of a respective said first and said second leg opening and towards a center crotch line.

15. The hygiene article of claim 14, wherein a tertiary elastic leg opening section of each of said first and said second leg opening sections is provided in a flat state prior to connection of said longitudinal side edge sections during manufacture, starting from a longitudinal side edge of said front part of the article, on a curve along a periphery of each said first and said second respective leg openings towards a center crotch line.

16. The hygiene article of claim 15, wherein a secondary elastic leg opening section is disposed between said primary elastic leg opening section and said tertiary elastic leg opening section.

17. The hygiene article of claim 16, wherein said secondary elastic leg opening section is elastified by thread- or band-shaped elastification means, which are disposed parallel to a central longitudinal axis of the article.

18. The hygiene article of claim 16, wherein respective end regions of said secondary elastic leg opening section are spaced apart from respective end areas of said primary and/or said tertiary elastic leg opening section by a length A, wherein A is at least 10 mm.

19. The hygiene article of claim 16, wherein elastification means of said secondary elastic leg opening section are fixed to said top sheet and/or said back sheet of said absorbent body.

20. The hygiene article of claim 19, wherein elastification means of said secondary elastic leg opening section are fixed in a fold of said back sheet.

21. The hygiene article of claim 16, wherein a longitudinal extension of said first and said second elastic cuff element sections is larger than a longitudinal extension of a separation between said primary elastic leg opening section and said tertiary elastic leg opening section by at most 8 cm.

* * * * *